United States Patent [19]

Heid et al.

[11] 3,999,942
[45] Dec. 28, 1976

[54] N-ACYLOYL-N-ALKYL-ALKYLENEDIAMINES AS DYE LEVELERS

[75] Inventors: Christian Heid, Frankfurt am Main; Karl-Heinz Keil, Offenbach am Main; Joachim Ribka, Offenbach am Main-Burgel; Otto Trösken, Frankfurt am Main; Gerhard Weckler, Sulzbach; Siegfried Wirth, Rosbach, all of Germany

[73] Assignee: Cassella Farbwerke Mainkur Aktiengesellschaft, Frankfurt am Main-Fechenheim, Germany

[22] Filed: Apr. 17, 1975

[21] Appl. No.: 569,065

Related U.S. Application Data

[62] Division of Ser. No. 501,291, Aug. 28, 1974, abandoned.

[30] Foreign Application Priority Data

Aug. 1, 1974 Germany .......................... 2437031

[52] U.S. Cl. .................................. 8/169; 8/172 R
[51] Int. Cl.² .................................. D06P 1/645
[58] Field of Search .......... 8/172, 169; 260/281 N, 260/281 GN, 78 UA

[56] References Cited

UNITED STATES PATENTS

| 2,526,948 | 10/1950 | Himel | 106/155 |
|---|---|---|---|
| 2,713,583 | 7/1955 | Smith | 8/85 |
| 3,078,138 | 2/1963 | Miller et al. | 8/128 A |
| 3,096,139 | 7/1963 | Hendle | 8/21 A |
| 3,556,715 | 1/1971 | Schmitt | 8/172 |
| 3,574,513 | 4/1971 | Wolf | 8/172 |

*Primary Examiner*—Donald Levy
*Attorney, Agent, or Firm*—Connolly and Hutz

[57] ABSTRACT

N-Acyloyl-N'-alkyl-alkylenediamines of the formula

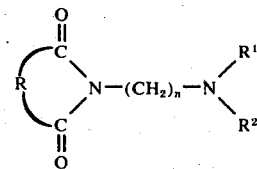

are prepared by reacting N-alkyl alkylenediamines with a derivative of a di-carboxylic acid. The compounds and their salts are useful as levelling auxiliaries for the dyeing of polyacrylonitrile or polyester with basic dyestuffs. Advantageously, the compounds are employed in conjunction with a non-ionic dispersing agent, for example a polyethoxylated fatty alcohol, and a solvent to give an electrolyte-insensitive dye bath.

5 Claims, No Drawings

N-ACYLOYL-N-ALKYL-ALKYLENEDIAMINES AS DYE LEVELERS

CROSS REFERENCE TO RELATED APPLICATION

This application is a division of application Ser. No. 501,291 filed Aug. 28, 1974 and now abandoned.

The invention relates to N-acrylon-N'-alkyl-alkylenediamines of the general formula I:

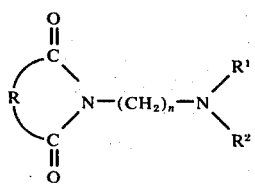

wherein R denotes a divalent aliphatic, cycloaliphatic, aromatic or bicyclic radical which together with the dicabonylamino group forms a 5-membered, 6-membered or 7-membered ring, $R^1$ denotes hydrogen or an alkyl radical with 8 to 12 C atoms, $R^2$ denotes an alkyl radical with 8 to 22 C atoms and n denotes the number 2, 3, 4, 5 or 6, and to processes for their preparation.

In the compounds of the general formula I, the carbon chain of the radical $R^2$ can be interrupted by sulphur, by the group -NH- or, preferably, by oxygen.

In the general formula I, the radical R can in particular represent the following divalent radicals:

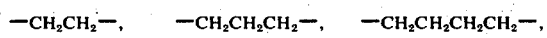

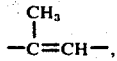

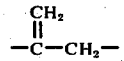

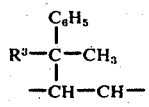

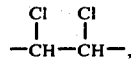

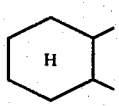

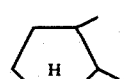

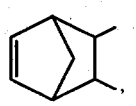

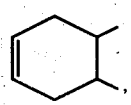

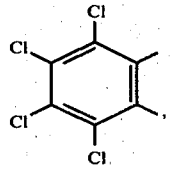

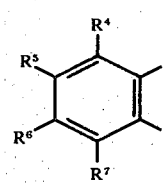

with $R^4$, $R^5$, $R^6$ and $R^7$ = hydrogen or alkyl with 1 to 6 C atoms,

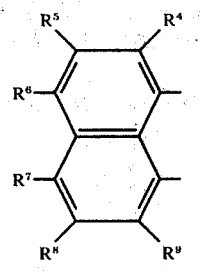

with $R^4$, $R^5$, $R^6$, $R^7$, $R^8$ and $R^9$ = hydrogen or alkyl with 1 to 6 C atoms,

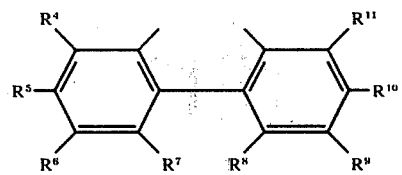

with $R^4$ to $R^{11}$ = hydrogen or alkyl with 1 to 6 C atoms.

$R^2$ preferably denotes tallow fat alkyl and n preferably denotes the number 3.

Compounds of the general formula I can be prepared by reacting a N-alkyl-alkylenediamine of the general formula II:

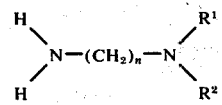

with an acylating agent of the general formula III:

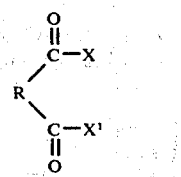

wherein R, $R^1$, $R^2$ and n have the meaning already mentioned and X and $X^1$ denote Cl, Br, OH or $OR^{13}$ (with $R^{13}$ = alkyl with 1 to 4 C atoms), or X and $X^1$ in the formula III together denote -O-. Normally, X and $X^1$ have the same meaning or together represent -O-. The acylating agents of the general formula III are in that case acid chlorides, acid bromides, alkyl esters or anhydrides of dicarboxylic acids of the general formula IV:

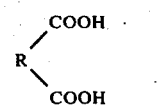

or these dicarboxylic acids themselves.

The dicarboxylic acids of the general formula IV are known. In particular, the following dicarboxylic acids or the acid bromides, acid chlorides, alkyl esters or anhydrides derived therefrom can be used for the preparation of the compound of the general formula I: succinic acid, glutaric acid, adipic acid, maleic acid, citraconic acid, itaconic acid, 1,2-dichlorosuccinic acid, alkyl-substituted succinic acids of the formula

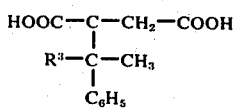

with $R^3$ = H or $CH_3$,
1,2-cyclohexane-dicarboxylic acid, 1,2-cyclopentanedicarboxylic acid, phthalic acid, tetrachlorophthalic acid, tetrahydrophthalic acid, alkylated phthalic acids of the formula

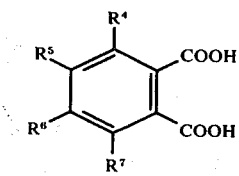

with $R^4$ to $R^7$ = alkyl with 1 to 6 C atoms, naphthalic acid, alkylated naphthalic acids of the formula

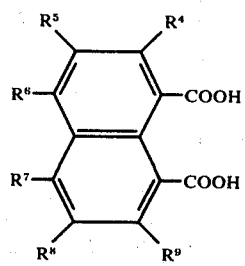

with $R^4$ to $R^9$ = alkyl with 1 to 6 C atoms, endomethylenetetrahydrophthalic acid, diphenic acid and alkylated diphenic acids of the formula

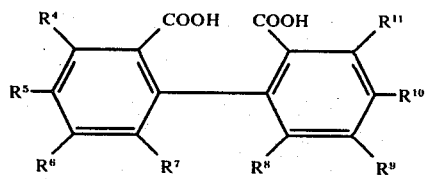

with $R^4$ to $R^{11}$ = alkyl with 1 to 6 C atoms.

The anhydrides of the abovementioned alkyl-substituted succinic acids can be prepared by reaction of a hydrocarbon of the general formula V, wherein $R^3$ = H or $CH_3$, with maleic anhydride (formula VI) at reaction temperatures of 120°– 170° in the presence of peroxide, for example $Na_2O_2$ or benzoyl peroxide.

The other dicarboxylic acids mentioned are well-known compounds from which the acid chlorides, acid bromides, anhydrides and esters can be synthesised according to the methods generally known for the preparation of such compounds.

N-alkyl-alkylenediamines of the general formula II in which n = 3 can easily be prepared by addition reaction of an amine of the general formula $HNR^1R^2$ at the C—C double bond of acrylonitrile and reduction of the nitrile group of the intermediate product to an amino group.

Compounds of the general formula II can also be prepared by alkylating the diamines of the general formula $H_2N(CH_2)_nNH_2$ in a known manner with alkylating agents. Examples of suitable alkylating agents are alkyl chlorides of the formula Cl-$R^2$. This gives compounds of the formula $H_2N(CH_2)_nNHR^2$. These compounds can be acylated, for example acetylated, and subsequently alkylated with an alkylating agent, for example an alkyl chloride of the formula Cl-$R^1$. After splitting off the acyl group, compounds of the general formula II are obtained, in which both $R^2$ and $R^1$ denote an alkyl radical of the type already mentioned.

The reaction of the N-alkyl-alkylenediamine of the general formula II with the acylating agent of the general formula III is preferably carried out in a suitable inert solvent. Examples of suitable solvents are aliphatic and aromatic hydrocarbons, for example xylene, toluene, decalin, tetralin and the like. The reaction is normally carried out at temperatures of 80° to 180° C and is in general complete after 1 to 3 hours. The reaction products produced in the reaction, namely water in the case of the acylation with the free dicarboxylic acids or the anhydrides and a lower alcohol in the case of the acylation with an ester, are preferably distilled continuously from the reaction mixture. When acylating with dicarboxylic acid anhydrides it has proved particularly desirable to carry out the reaction at 140°–150° C. The preferred temperature range for the acylation with the esters is 120° to 130° C whilst with the free acids it is 120° C. To complete the reaction it can be necessary, especially in the case of the acylation with the free acids, to carry out a post-condensation at temperatures of 100° to 110° C for 1 to 2 hours under reduced pressure, suitably under a pressure of 20 to 25 mm Hg, that is to say to distil off reaction products formed, such as water or alcohol.

The compounds of the general formula I are normally yellow-brown waxy highly viscous products without an accurately defined melting point, which, surprisingly, are suitable for use as temporary retarders with an astonishingly low permanence and high leveling capacity, as auxiliaries for dyeing polyacrylonitrile or polyesters with basic dyestuffs.

Fibre structures consisting of polyacrylonitrile or acid-modified polyesters can be dyed with basic dyestuffs. However, if levelling auxiliaries are not added, there is the danger, especially in the case of light shades, that uneven dyeings are obtained. In order

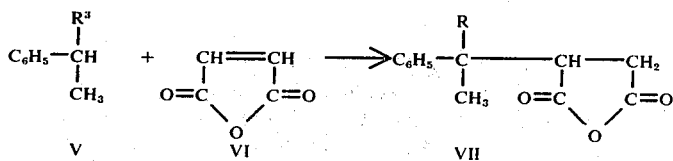

nevertheless to obtain even dyeings when dyeing the said fibres with basic dyestuffs, it is necessary to employ special levelling auxiliaries, so-called retarders. For example, a process is known for the level dyeing of polyacrylonitrile structures, in which quaternary alkoxy-alkyl-ammonium compounds (DAS No. 1,123,286) are used as retarders. However, in general compounds with long-chain hydrophobic hydrocarbon radicals have the decisive disadvantage that in the case of an inadvertent overdose they tenaciously reserve the polyacrylonitrile fibres which are to be dyed and make it practically impossible to achieve the desired depth of colour or shade. Levelling auxiliaries with such properties are called permanent retarders. In order to avoid such mis-dyeings and dyestuff losses, the more easily employed temporary retarders, for example benzylpyridinium chloride (U.S. Pat. No. 2,986,444) are frequently used. Temporary retarders are easily handled in use. They make it possible, even in the case of an inadvertent overdose, to achieve good exhaustion of the liquor within the customary dyeing time, and to achieve the desired depth of colour. However, they have the decisive disadvantage that when employed in the same amounts they are less effective than the permanent retarders. It has now been found, surprisingly and in no way foreseeably, that the compounds of the general formula I combine in themselves both the outstanding levelling capacity of the permanent retarders and the low permanence of the temporary retarders. They are outstandingly active as levelling auxiliaries in all dyeings of structures consisting of polyacrylonitrile, copolymers containing acrylonitrile or acid-modified polyester fibres, and are preferably employed in the form of the salts of the general formula VIII:

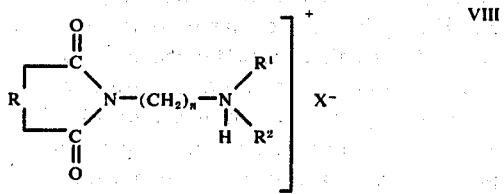

VIII as approx. 50 per cent strength solutions or dispersions.

In the general formula VIII, R, $R^1$, $R^2$ and n have the meanings already indicated and $X^-$ denotes the anion of an inorganic acid or of a carboxylic acid. In particular, $X^-$ can represent the following anions: $PO_4^{3-}$, $SO_4^{2-}$, $NO_3^-$, $Cl^-$, $HCOO^-$, $CH_3COO^-$ and $C_2H_5COO^-$. The acetate anion is preferred.

The salts of the general formula VIII are prepared by mixing the compounds of the general formula I with the calculated amounts of acids.

Examples of possible solvents or dispersing agents for the compounds of the general formula I or their salts of the general formula VIII are water or isopropanol, and for salts of the general formula VIII acids, especially formic acid and acetic acid, can also be used.

The dyeings can be effected with basic dyestuffs, for example basic azo dyestuffs and anthraquinone dyestuffs, induline, cyanine and methine dyestuffs, quinoline and acridine dyestuffs, and dyestuffs of the diarylmethane or triarylmethane, oxazine, thiazine and diazine series. In general, the process used is that the goods to be dyed are introduced, using a liquor ratio of 1 : 3 to 1 : 200, especially of 1 : 10 to 1 : 20, into a dye bath which has been brought to the boil. The dye bath contains the above-mentioned dyestuffs and 0.01 to 5 g/liter, especially 0.025 to 3.5 g/liter, of the compounds of the general formula I, preferably in the form of the salts of the general formula VIII. For example, using a liquor ratio of 1:3 the concentration of the compounds of the general formula I or of their salts is 0.8 to 3.5 g/l, whilst using a liquor ratio of 1 : 100 it is 0.025 to 0.1 g/l.

The compounds of the general formula I or their salts are preferably introduced into the dye bath as approx. 50% strength solutions or dispersions.

Examples of solvents or dispersing agents which can be used are water, isopropanol or an acid, especially acetic acid. The dyeing can be effected in the usual manner in the presence of additives, such as, for example, acids, for example formic acid and acetic acid. Equally, it is possible to use mixtures of the substances claimed according to the invention.

In some cases it has now been found that the active compounds of the general formula I or VIII, when used as levelling auxiliaries, display a degree of sensitivity to electrolytes. Major amounts of salt, for example of sodium sulphate and sodium chloride, such as are, for example, introduced into the dyeing liquor as extenders for dyestuffs, can cause flocculation of the active compounds. However, the sensitivity of the active compounds to electrolytes can be eliminated in a simple manner by employing the active compounds as a mixture with non-ionic dispersing agents. Examples of suitable non-ionic dispersing agents are ethoxylation products of alkylphenols (for example nonylphenol) reacted with 8 to 20 moles ethylene oxide), ethoxylation products of higher fatty acids, fatty acid amides or fatty alcohols. Higher fatty acids and fatty alcohols suitable for the ethoxylation are those containing 7 to 30 C atoms, such as occur, for example, in natural fats and oils, for example wool grease. Higher fatty acid amides suitable for ethoxylation are those with 12 to 20 C atoms in the molecule. The degree of ethoxylation of suitable products is normally 8 to 90, preferably 10 to 80, that is to say the products have been prepared from 1 mol of fatty acid, fatty alcohol and/or fatty acid amide and 8 to 90 mols, preferably 10 to 80 mols, of ethylene oxide. Particularly suitable dispersing agents are those which have been prepared by reaction of stearyl alcohol, oleyl alcohol and/or coconut fatty alcohol with 25 mols of ethylene oxide. Reaction of mixtures of fatty acids, fatty alcohols and/or fatty acid amides also gives suitable non-ionic dispersing agents.

A suitable electrolyte-insensitive ready-to-use preparation of the levelling auxiliary consists, for example, of a solution or dispersion of the following composition: 40 to 60% by weight, preferably 50% by weight, of active compound (compound of the formula I and/or VIII), 1 to 10% by weight, preferably 1 to 5% by weight, of non-ionic dispersing agent, in particular ethoxylated stearyl alcohol, oleyl alcohol or coconut fatty alcohol, remainder: solvents (water, isopropanol, glacial acetic acid or formic acid).

A preparation of the active compound in this form has proved in practice to be completely insensitive to electrolyte. Mixtures of non-ionic dispersing agents and/or solvent mixtures and/or mixtures of active compounds can also be used to produce the preparation.

In the examples which follow the temperatures are given in degrees centigrade, the percentages in percentages by weight and the parts in parts by weight.

EXAMPLE 1

70 g (0.7 mol) of succinic anhydride are introduced over the course of approx. 1 hour into a melt of 223 g (0.6 mol) of tallow fat propylenediamine at a temperature of 80° – 85° C and the mixture is heated to 160° over the course of 1 hour. It is then condensed for two hours at an internal temperature of 150° – 160° C and the resulting water of reaction is distilled off continuously. Finally, the residual water of reaction is distilled off in vacuo at 105° to 110°. The resulting yellow-brown viscous product has the formula:

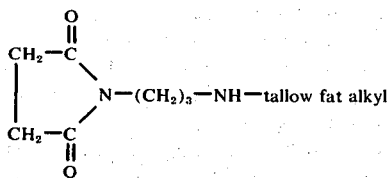

The product gives a clear solution in glacial acetic acid and is employed industrially in the form of the following preparation: 50 parts by weight of the reaction product are fused at 50° – 60° with 5 parts by weight of a dispersing agent which has been prepared by reaction of stearic acid amide with 10 mols of ethylene oxide, and the product is dissolved in 45 parts of glacial acetic acid.

Analysis: Molecular weight approx. 452, N calculated: 6.2% Found: 6.0%

Analogously, 214 g (0.6 mol) of tallow fat ethylenediamine or 230 g (0.6 mol) of tallow fat butylenediamine or 247 g (0.6 mol) of tallow fat hexylenediamine are reacted with 70 g (0.7 mol) of succinic anhydride. The corresponding products are also readily soluble in glacial acetic acid and can be employed as approx. 50 percent strength solutions in glacial acetic acid. In the same way, 185 g (0.5 mol) of tallow fat propylenediamine can be reacted with 52 g (0.53 mol) of maleic anhydride.

EXAMPLE 2

84.5 g (0.65 mol) of itaconic acid are introduced into a melt of 223 g (0.6 mol) of tallow fat propylenediamine at 95° to 100° C. The mixture is then heated for half an hour at 110° to 115° C and two hours at 120° C and the water produced is subsequently distilled off in vacuo. The resulting dark brown mass has the formula

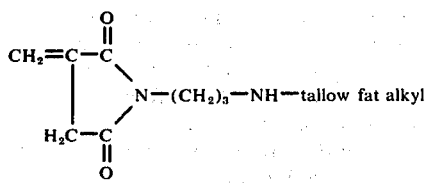

Analysis: Molecular weight: 480 N calculated: 5.8% Found: 6.0%

The product gives a clear solution in glacial acetic acid and is used industrially for dyeing, for example in the following form: 50 parts by weight of the reaction product obtained are fused at 50° to 60° with 7.5 parts of a dispersing agent which has been prepared by reaction of oleyl alcohol with 20 mols of ethylene oxide, and this melt is dissolved in a mixture of 20 parts by weight of i-propanol and 32.5 parts by weight of glacial acetic acid. Using this preparation of the compound mentioned, a good levelling action is achieved when dyeing polyacrylonitrile structures with basic dyestuffs.

EXAMPLE 3

34.5 g (0.233 mol) of phthalic anhydride are introduced over the course of 1 hour into a melt of 41 g (0.22 mol) of N-octyl-propylenediamine at 80° – 90° C and the mixture is stirred further for 20 minutes at 100° – 110° C and heated to 140°– 150° C over the course of 1.5 hours. The condensation is then continued for 2 hours at 140° to 150° C and the water of reaction is continuously distilled off during the reaction. The last remnants of water are removed in a waterpump vacuum at 100° – 110° C. The brown viscous mass has the formula

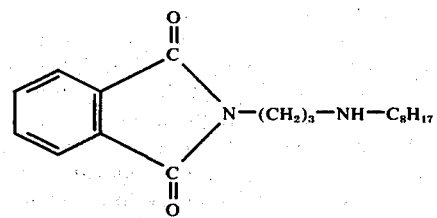

Analysis: Molecular weight: approx. 136 N calculated: 8.8% Found: 8.2%

The product gives a clear solution in glacial acetic acid. Fusing 50 parts of this product with 3 parts by weight of a reaction product of stearyl alcohol with 25 mols of ethylene oxide at a temperature of 60° to 80° and dissolving this melt in a mixture of 27 parts by weight of glacial acetic acid and 20 parts by weight of i-propanol gives a mixture which is stable in batches containing electrolytes. Using this composition, prefect level dyeings can be achieved on polyacrylonitrile fibres with basic dyestuffs.

In the same manner, 39 g (0.18 mol) of N-decyl-propylenediamine are reacted with 29 g (0.196 mol) of phthalic anhydride, 38 g (0.127 mol) of N,N-dioctyl-propylenediamine are reacted with 20.7 g (0.14 mol) of phthalic anhydride, 42.8 g (0.125 mol) of N,N-dilaurylethylenediamine are reacted with 20.7 g (0.14 mol) of phthalic anhydride or 163 g (0.5 mol) of N-octadecylpropylenediamine are reacted with 74 g (0.5 mol) of phthalic anhydride. Products of the following formulae are thus obtained:

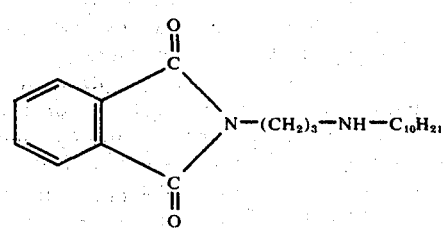

-continued

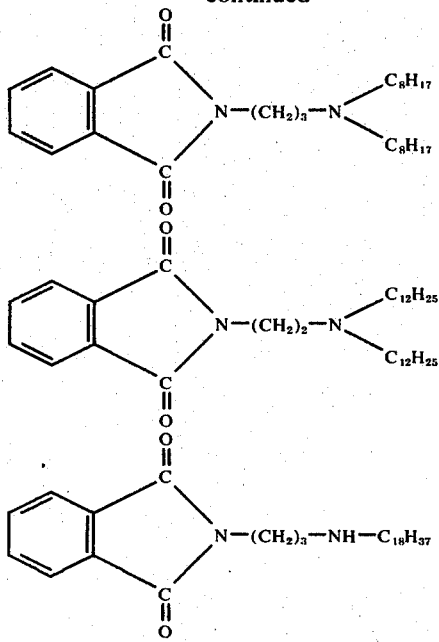

The resulting products are brown and viscous and dissolve very readily in glacial acetic acid. They are used in the form of a solution, as preparations containing 50 parts by weight of the particular reaction product, 5 parts by weight of a dispersing agent, which has been prepared by reaction of stearyl alcohol with 80 mols of ethylene oxide, and 45 parts by weight of glacial acetic acid.

These mixtures are distinguished by high stability, above all to sodium sulphate and sodium chloride, which are frequently present as extenders in dyestuffs.

EXAMPLE 4

24 g (0.16 mol) of phthalic anhydride are introduced into a melt of 41.5 g (0.149 mol) of N-isononyloxypropyl-propylenediamine at 90° to 100° C. The mixture is then heated for a further hour at 100° to 110° C and thereafter heated up to 150° – 155° C over the course of 15 minutes, the condensation is continued for 2 hours at 150° to 155° C and the water of reaction is distilled off continuously. The last remnants of water are removed in vacuo at 100° to 110° C. The resulting yellow-brown and viscous product, of the formula

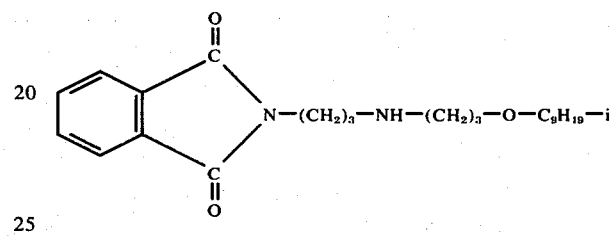

gives a clear solution in glacial acetic acid.

In the same manner, 38.5 g (0.124 mol) of N-isotridecyloxypropyl-propylenediamine or 39,2 g (0.124 mol) of N-isotridecyl-mercaptopropyl-propylenediamine are reacted with 20.3 g (0.137 mol) of phthalic anhydride, and 48.1 g (0.125 mol) of N-octadecyl-aminoproply-propylenediamine or N-octadecyl-aminoethyl-ethylenediamine are reacted with 23.2 g (0.137 mol) of naphthalic anhydride under the reaction conditions mentioned. This gives products of the following formulae:

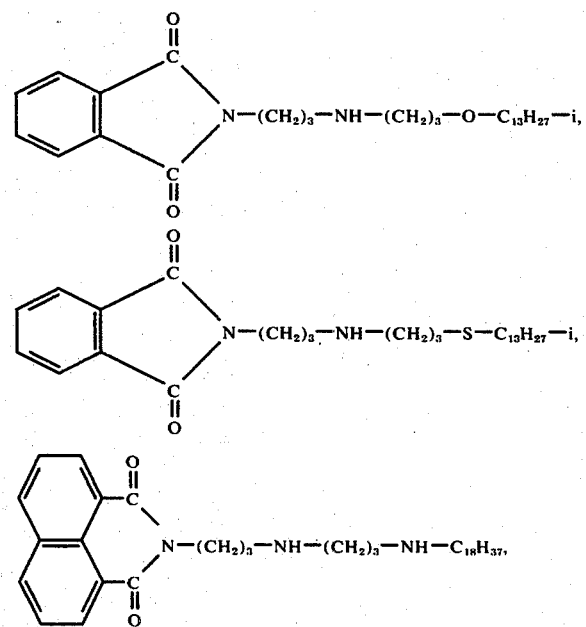

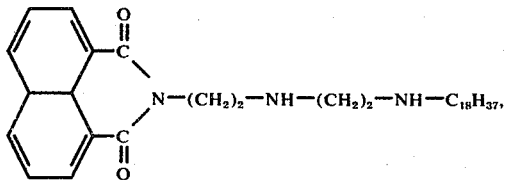

EXAMPLE 5

119 g (0.6 mol) of naphthalene-1,8-dicarboxylic acid anhydride (naphthalic anhydride) are introduced into a melt of 185 g (0.5 mol) of tallow fat alkyl-propylenediamine at 90° to 95° C. The mixture is then heated to 140° – 150° C over the course of 1 hour and condensed at 140° to 150° C for 2 hours, and the water produced is distilled off continuously. The resulting brown-yellow mass, of the formula

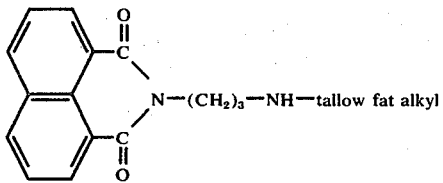

gives a clear solution in glacial acetic acid and has a good levelling action when dyeing polyacrylonitrile structures with basic dyestuffs.

Analysis: Molecular weight: approx. 550 N calculated: 5.1% Found: 4.9%

EXAMPLE 6

80.6 g (0.53 mol) of tetrahydrophthalic anhydride are introduced into a melt of 185 g (0.5 mol) of tallow fat alkyl-propylenediamine at 90° to 100° C and the mixture is heated to 150° – 160° C over the course of 1 hour. It is then condensed for 2.5 hours at this temperature and the water is distilled off continuously.

A brown viscous product of the formula

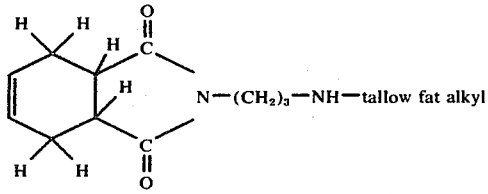

which gives a clear solution in glacial acetic acid, is obtained.

Under the same reaction conditions, 185 g (0.5 mol) of tallow fat alkyl-propylenediamine are reacted with 87 g (0.53 mol) of endomethylenetetrahydrophthalic anhydride to give a product of the formula

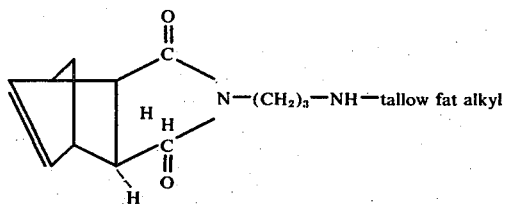

which also gives a clear solution in glacial acetic acid.

EXAMPLE 7

In a laboratory dyeing apparatus, 10 g of polyacrylonitrile yarn are introduced, using a liquor ratio of 1 : 40, into a bath warmed to 98° C which contains, per liter, 0.075 g of the commercially available dyestuff

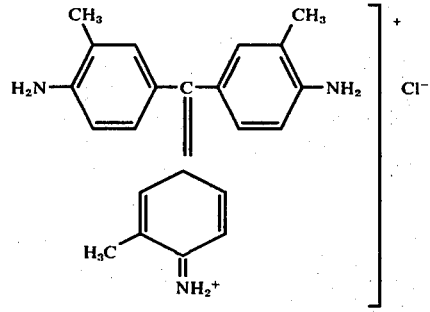

0.225 ml of glacial acetic acid and 0.45 g of an approx. 50 per cent strength solution of the compound of the formula

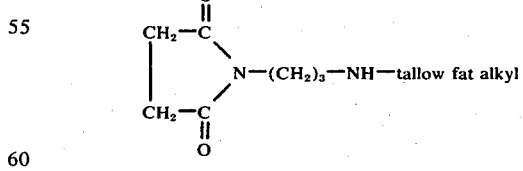

5 parts by weight of a reaction product of 1 mol of stearyl alcohol with 40 mols of ethylene oxide and 45 parts by weight of glacial acetic acid.

Dyeing is carried out for 90 minutes at 98° C and a perfect, level red-violet dyeing is obtained. Comparably good results are obtained with similar preparations of the following compounds:

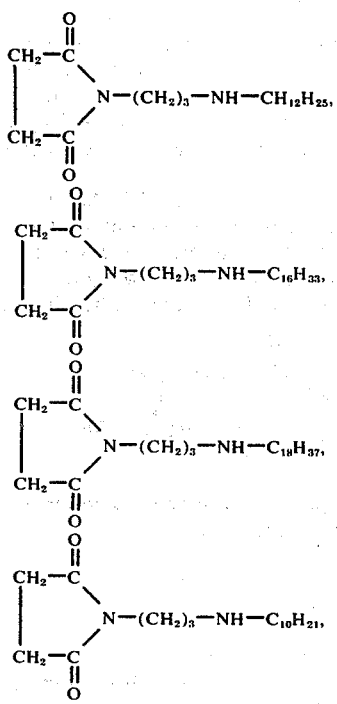

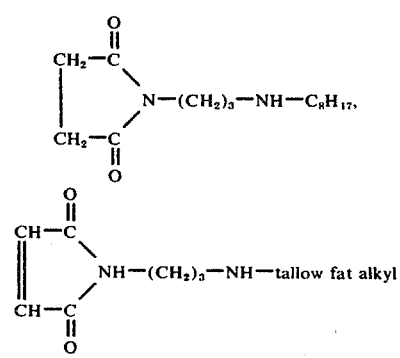

EXAMPLE 8

If, in the process described in Example 7, the dyestuff mentioned there is replaced by 0.1 g of the commercially available dyestuff

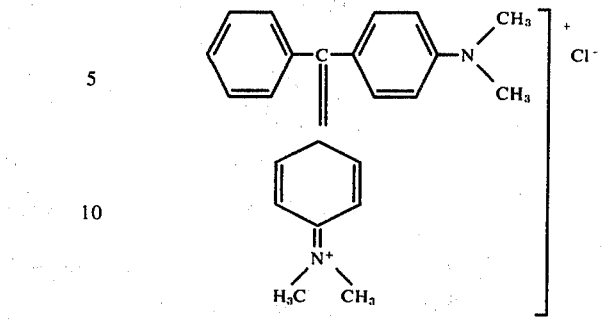

and the auxiliaries mentioned there are replaced by the products of Example 3 in the same concentration, green dyeings of excellent evenness are obtained, with good exhaustion of the bath.

EXAMPLE 9

If, in the process described in Example 7, the dyestuff mentioned there is replaced by 0.5 g of the commercially available dyestuff

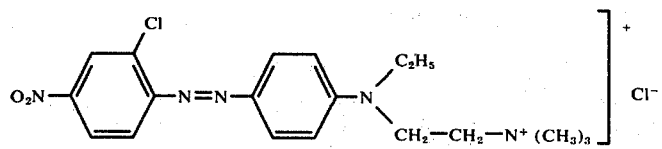

and the auxiliaries mentioned there are replaced by products of Example 4 in the same concentration, very level red dyeings are obtained.

EXAMPLE 10

If, in the process described in Example 7, the dyestuff mentioned there is replaced by 0.5 g of the dyestuff

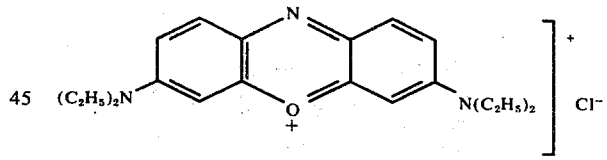

and 0.225 ml of glacial acetic acid and 0.45 g of a product described in Example 6, as an approx. 50% strength mixture with a dispersing agent in glacial acetic acid is added, very level blue dyeings are obtained, using a dyeing time of 90 minutes. Without the auxiliaries mentioned, on the other hand, the dyeings turn out blotchy.

What is claimed is:

1. A composition comprising (a) 40 to 60% by weight of a levelling auxiliary selected from the group consisting of N-acyloyl-N'-alkyl-alkylenediamines of the formula

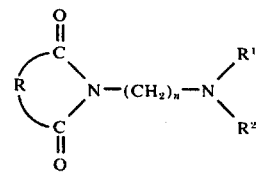

and the salts thereof wherein R is selected from the group consisting of —CH$_2$CH$_2$—; —CH$_2$CH$_2$CH$_2$—; —CH$_2$CH$_2$CH$_2$CH$_2$—; —CH=CH—;

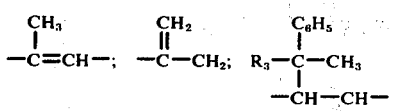

wherein R$^3$ is H or CH$_3$,

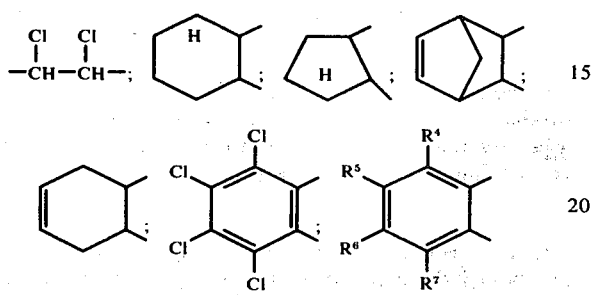

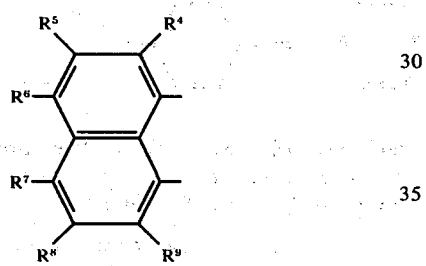

wherein R$^4$, R$^5$, R$^6$ and R$^7$ are each hydrogen or alkyl having 1 to 6 carbon atoms;

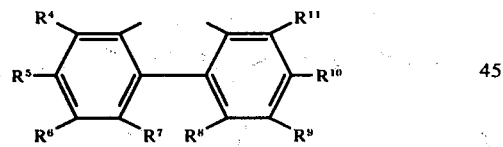

wherein R$^4$, R$^5$, R$^6$, R$^7$, R$^8$ and R$^9$ are each hydrogen or alkyl having 1 to 6 carbon atoms and wherein R$^4$ to R$^{11}$ are hydrogen or alkyl having 1 to 6 carbon atoms;
R$^1$ is hydrogen or alkyl having 8 to 12 carbon atoms; R$^2$ has from 8 to 22 carbon atoms and is alkyl, alkyloxyalkyl, alkylthioalkyl or alkylaminoalkyl and n is an integer from 2 to 6 inclusive; (b) 1 to 10% by weight of a non-ionic dispersing agent and (c) a balance to 100% of a solvent.

2. The composition of claim 17 wherein the levelling auxiliary is present in an amount of about 50% by weight and the non-ionic dispersing agent is present in an amount of from 1 to 5% by weight.

3. The composition of claim 1 wherein R is

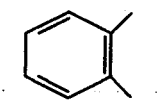

4. The composition of claim 1 wherein the levelling auxiliary is the compound

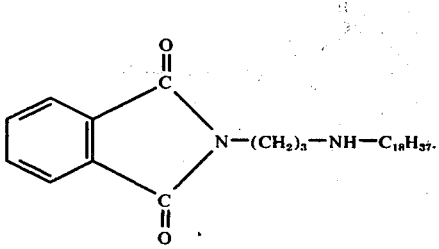

5. The composition of claim 1 comprising
a. 50 parts by weight of

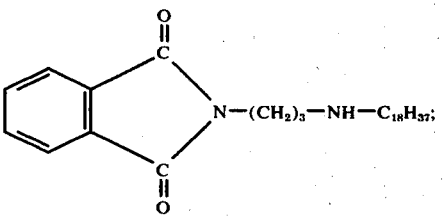

b. 5 parts by weight of ethoxylated stearyl alcohol and
c. 45 parts by weight of glacial acetic acid.

* * * * *